US006993376B2

(12) United States Patent
Testardi

(10) Patent No.: US 6,993,376 B2
(45) Date of Patent: Jan. 31, 2006

(54) RADIATION MEASUREMENT WITHIN THE HUMAN BODY

(76) Inventor: Louis R. Testardi, 1803 Sageway Dr., Tallahassee, FL (US) 32303

( * ) Notice: Subject to any disclaimer, the term of this patent is extended or adjusted under 35 U.S.C. 154(b) by 619 days.

(21) Appl. No.: 10/084,163

(22) Filed: Feb. 28, 2002

(65) Prior Publication Data

US 2003/0163016 A1 Aug. 28, 2003

Related U.S. Application Data

(63) Continuation-in-part of application No. 10/056,113, filed on Jan. 28, 2002, now abandoned.

(51) Int. Cl.
*A61B 6/00* (2006.01)
*G01R 23/02* (2006.01)
(52) U.S. Cl. ............ 600/478; 600/476; 600/477; 600/436; 250/370.07
(58) Field of Classification Search ........... 250/306, 250/308, 336.1, 358.1, 360.1, 361, 366–370.1, 250/371, 390, 391–392, 458.1, 459.1, 302; 600/407, 436, 475, 478; 378/44, 64–65, 378/97; 424/9.3
See application file for complete search history.

(56) References Cited

U.S. PATENT DOCUMENTS

| 4,932,412 A | | 6/1990 | Goldenberg |
| 5,704,890 A | | 1/1998 | Bliss et al. |
| 5,811,814 A | * | 9/1998 | Leone et al. ............ 250/368 |
| 5,880,475 A | | 3/1999 | Oka et al. |
| 5,905,263 A | * | 5/1999 | Nishizawa et al. ...... 250/368 |
| 6,151,769 A | | 11/2000 | Bliss et al. |
| 6,231,513 B1 | * | 5/2001 | Daum et al. ............ 600/458 |
| 2002/0087079 A1 | * | 7/2002 | Kaufman et al. ........ 600/436 |

FOREIGN PATENT DOCUMENTS

| JP | 02206786 A | * | 8/1990 |
| JP | 10-213663 A1 | | 8/1998 |
| JP | 2001-56381 A1 | | 2/2001 |

OTHER PUBLICATIONS

U.S. NRC Report NUREG/CR-5223 entitled "Scintillat-Ing Fiber Detector for In-Vivo Endoscopic Internal Dosimetry", published Oct. 1988.
Phys. Med. Biol., 1992, vol. 37 No. 10, pp. 1883-1900, entitled "Water-equivalent plastic scintillation detectors for high-energy beam dosimetry".

* cited by examiner

*Primary Examiner*—Brian L Casler
*Assistant Examiner*—Baisakhi Roy
(74) *Attorney, Agent, or Firm*—David A. Testardi

(57) ABSTRACT

A displacement difference dosimetry method is provided for use with in-vivo scintillating fiber radiation detectors. A scintillating fiber includes an insertion end which is incrementally inserted into a human body using a catheter or hypodermic needle to provide a fixed (but not necessarily known) insertion path. A photomultiplier tube is coupled to the other end of the scintillating fiber and detects both scintillation light and any Cerenkov light for each position of the scintillating fiber insertion end along the fixed insertion path. The change in the amount of light detected by the photomultiplier tube divided by the corresponding amount of change in position of the scintillating fiber insertion end gives a measure of the dose rate at the scintillation fiber tip which is substantially free from the effects of Cerenkov light.

34 Claims, 1 Drawing Sheet

RADIATION MEASUREMENT WITHIN THE HUMAN BODY

CROSS-REFERENCE TO RELATED PATENT APPLICATION

This application is a continuation-in-part of application Ser. No. 10/056,113, filed on Jan. 28, 2002, now abandoned, by the inventor hereof and entitled "RADIATION MEASUREMENT WITHIN THE HUMAN BODY", the specification of which is incorporated by reference herein.

BACKGROUND OF THE INVENTION

1. Field of the Invention

The present invention pertains to the field of radiation measurement within the human body. More particularly, the present invention pertains to the field of in-vivo dosimetry using a single scintillating fiber inserted into the human body for accurate radiation measurement.

2. Description of the Related Art

Radiation is often used in the treatment of human health problems. These problems, generally occurring "in-vivo", include cancer and, more recently, the re-closing of arteries after balloon angioplasty. Knowledge of radiation levels within the body, important for the success of such treatment, is usually pursued by calculation or modeling because direct measurement of internal body radiation is often too difficult to carry out.

In the field of radiation measurement within the human body, the following related art documents are known (all of which are incorporated herein by reference): U.S. Pat. No. 4,932,412 entitled "Intraoperative and Endoscopic Tumor Detection and Therapy"; U.S. Nuclear Regulatory Commission Report NUREG/CR-5223 entitled "Scintillating Fiber Detector for In-Vivo Endoscopic Internal Dosimetry", published October 1988; Phys. Med. Biol., 1992, Vol. 37 No. 10, pp. 1883–1900 entitled "Water-equivalent plastic scintillation detectors for high-energy beam dosimetry: I. Physical characteristics and theoretical considerations"; U.S. Pat. No. 5,704,890 entitled "Real Time Sensor for Therapeutic Radiation Delivery"; Japanese Published Unexamined Patent Application 10-213663 entitled "Local Dosimeter"; U.S. Pat. No. 5,880,475 entitled "Scintillation Fiber Type Radiation Detector"; U.S. Pat. No. 5,905,263 entitled "Depth Dose Measuring Device"; U.S. Pat. No. 6,151,769 entitled "Method of Making a Scintillator Waveguide"; and Japanese Published Unexamined Patent Application 2001-56381 entitled "Local Radiation Amount Measuring Device and Medical Device Equipped Therewith".

The systems noted above require special corrections or fiber assemblies to remove errors arising from Cerenkov radiation, which generally complicates the use of scintillating fibers for therapeutic radiation. Cerenkov radiation is the radiation that results when a charged particle, moving in some medium, travels faster than light does in that medium. (The charged particle can be introduced 'on its own', or can be an electron kicked out of an atom by an entering photon=gamma ray or X-ray.) The speed of light in a medium is given by its index of refraction. The speed of a particle is given by its mass and its energy. The index of refraction in most scintillating fiber materials is 1.6. Thus, an electron with energy more than about 0.14 MeV introduced on its own, or kicked out of an atom by an entering photon (=gamma ray) of energy more than about 0.28 MeV, will be travelling fast enough to generate Cerenkov radiation. Most High Dose Rate radioisotopes (e.g. Ir-192 and P-32, which are introduced into the body via a catheter or the like during HDR afterloader therapy), and all 'external X-Ray beam' sources, will have enough energy to trigger Cerenkov radiation. Low Dose Rate radioisotopes (e.g. I-125, Pd103) used in medical implant seed therapy may not emit anything with enough energy to trigger Cerenkov radiation.

Cerenkov radiation can occur in most scintillating fibers. In the prior art, there are two common ways to remove the errors arising from Cerenkov radiation. The first is to employ special filter assemblies within the measuring fiber to remove the Cerenkov light component (see e.g. FIG. 1 in JP 2001-56381 A). The second is to include an additional reference (or background) fiber, without a scintillating tip, which is exposed to the ambient radiation (see FIG. 1 in Phys. Med. Biol., 1992, Vol. 37 No. 10, at page 1886). The reference fiber also produces the Cerenkov light component which can then be subtracted from the output signal of the measuring fiber to produce a corrected signal substantially free of the Cerenkov light component.

A third way to remove the Cerenkov light component is mathematically. This way is preferred since physical modifications to the fiber assembly are not required and it can therefore lead to a simpler and cheaper way to perform in-vivo radiation dosimetry. However, previous attempts to mathematically model or predict the Cerenkov radiation component have required complex software to evaluate complex mathematical formulas and have also required a knowledge of the geometrical shape of the fiber path (see FIGS. 12 and 13, and sections [0062] to [0075], of JP 2001-56381 A).

SUMMARY OF THE INVENTION

It is a first object of the invention to provide high-resolution 1-dimensional, in-vivo dosimetry with a single, scintillating fiber. This fiber can be very small in diameter (e.g. 0.5 mm). This allows radiation measurement along any path in the human body that a 1 mm diameter needle (the standard blood sample needle size) or catheter can go.

It is a second object of the invention to provide automatic removal of the error from Cerenkov radiation in the use of scintillating fibers, without needing a knowledge of the geometrical shape of the fiber path or complex software, thereby providing a simpler and cheaper way to perform in-vivo dosimetry.

In one respect, the invention relates to a displacement difference dosimetry method for in-vivo measuring of dose rates within a radiation field, the method comprising the steps of:

a) providing a scintillating fiber having an insertion end and a coupling end;

b) coupling the coupling end of the scintillating fiber to a light intensity measuring device, the light intensity measuring device being located substantially outside of the radiation field and producing a voltage output in accordance with a measured light intensity from the scintillating fiber;

c) providing a guide channel having an insertion end and an external end;

d) inserting the insertion end of the guide channel into a human body to a region where radiation is to be measured, so as to provide a substantially fixed path into the human body;

e) inserting the insertion end of the scintillating fiber into the external end of the guide channel and into the human body along the substantially fixed path;

f) subjecting the region of the body at the insertion end of the scintillating fiber to radiation;

g) detecting the position $\Lambda$ of the insertion end of the scintillating fiber along the substantially fixed path within the human body and measuring the light intensity at the light intensity measuring device, with the measured light intensity representing both scintillation light from the scintillating fiber and also Cerenkov light;

h) incrementally displacing the insertion end of the scintillating fiber by a small distance $\Delta\Lambda$ to a new detected position $\Lambda+\Delta\Lambda$ along the substantially fixed path and measuring the light intensity at the light intensity measuring device, with the measured light intensity representing both scintillation light from the scintillating fiber and also Cerenkov light;

i) determining a radiation dose rate, substantially free from the effects of Cerenkov light, for an incremental segment from $\Lambda$ to $\Lambda+\Delta\Lambda$ along the substantially fixed path according to the expression:

$$\text{Dose Rate} = C \times \Delta V / \Delta \Lambda,$$

where C is a coefficient, $\Delta V$ is the change in voltage output of the light intensity measuring device which results from the insertion end of the scintillating fiber being moved between the positions $\Lambda$ and $\Lambda+\Delta\Lambda$, and $\Delta\Lambda$ is the amount of incremental displacement.

In another respect the invention relates to a displacement difference dosimetry method as described above wherein the voltage output produced by the light intensity measuring device varies substantially linearly in accordance with the dose rate of radiation hitting the scintillating fiber.

In still another respect the invention relates to a displacement difference dosimetry method for in-vivo measuring of dose rates within a radiation field, the method comprising the steps of:

a) providing a scintillating fiber having an insertion end and a coupling end;

b) coupling the coupling end of the scintillating fiber to a light intensity measuring device, the light intensity measuring device being located substantially outside of the radiation field and producing a voltage output which varies substantially linearly in accordance with a dose rate of radiation hitting the scintillating fiber;

c) providing a guide channel having an insertion end and an external end;

d) inserting the insertion end of the guide channel into a human body to a region where radiation is to be measured, so as to provide a substantially fixed path into the human body;

e) inserting the insertion end of the scintillating fiber into the external end of the guide channel and into the human body along the substantially fixed path;

f) subjecting the region of the body at the insertion end of the scintillating fiber to radiation;

g) detecting the positionl $\Lambda$ of the insertion end of the scintillating fiber along the substantially fixed path within the human body and measuring the light intensity at the light intensity measuring device;

h) incrementally displacing the insertion end of the scintillating fiber by a small distance $\Delta\Lambda$ to a new detected position $\Lambda+\Delta\Lambda$ along the substantially fixed path and measuring the light intensity at the light intensity measuring device;

i) determining a radiation dose rate for an incremental segment from $\Lambda$ to $\Lambda+\Delta\Lambda$ along the substantially fixed path according to the expression:

$$\text{Dose Rate} = C \times \Delta V / \Delta \Lambda,$$

where C is a coefficient, $\Delta V$ is the change in voltage output of the light intensity measuring device which results from the insertion end of the scintillating fiber being moved between the positions $\Lambda$ and $\Lambda+\Delta\Lambda$, and $\Delta\Lambda$ is the amount of incremental displacement; and after the radiation dose rate for the incremental segment from $\Lambda$ to $l+\Delta\Lambda$ along the substantially fixed path has been determined, repeatingly performing the following additional step to provide 1-dimensional radiation tomography:

j) incrementally displacing the insertion end of the scintillating fiber by an additional small distance, detecting the resulting change in position of the insertion end of the scintillating fiber and measuring the corresponding light intensity from the scintillating fiber at the light intensity measuring device, and determining a new radiation dose rate for an additional incremental segment along the substantially fixed path according to the Dose Rate expression.

In each case, the coefficient C may be equal to 1 (thus yielding a relative Dose Rate expression) or may be a derived calibration coefficient (thus yielding an absolute Dose Rate expression). The guide channel may be a catheter, hypodermic needle, or similar device.

The invention will, however, be best understood by a perusal of the following description in conjunction with the accompanying drawing, in which:

DETAILED DESCRIPTION OF THE PREFERRED EMBODIMENTS

Figure 1:
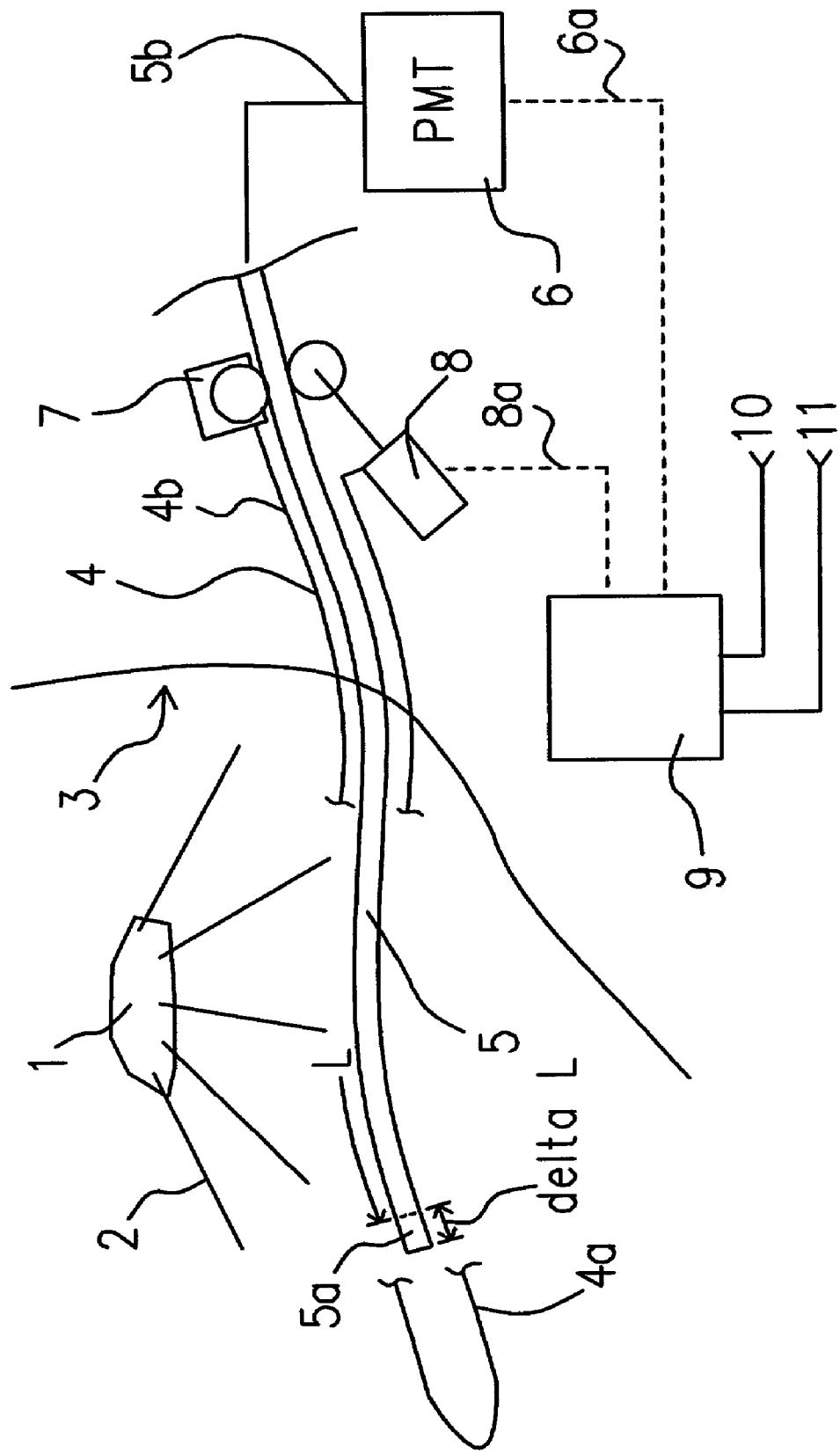
FIG. 1 is a schematic representation of an in-vivo dosimetry method according to the preferred embodiments of the invention using a single scintillating fiber inserted into the human body.

Referring now to FIG. 1, there is shown schematically a radiation source 1 producing a radiation field 2 within a human body, the outline of which is indicated at 3. The radiation source 1 may comprise an internal or external High Dose Rate source (such as are used in HDR afterloader therapy or external beam therapy), an internal Low Dose Rate source (such as an implanted brachytherapy seed or radio-pharmaceuticals), or any other radiation source used in treating the human body. A guide channel 4 (such as a catheter or hypodermic needle having an internal diameter of between 0.3 and 1.1 mm and an external diameter of between 0.4 mm and 1.5 mm, shown only partially in FIG. 1) is inserted into the human body 3 and passes in the vicinity of the radiation field 2. The guide channel 4 (which provides very little or no radiation shielding) has an insertion end 4a (which is inserted into the human body) and an external end 4b (which remains outside of the human body). The position of the insertion end 4a of the guide channel 4 within the human body 3 can be determined using standard X-ray or ultrasound techniques, and the guide channel 4 provides a fixed (or substantially fixed) path into the human body 3. A single, continuous, flexible scintillating fiber 5 having a sub-mm diameter and one or more cladding layers (for preventing, or greatly reducing, the loss of optical light within the fiber to its surroundings) is inserted into the guide channel 4 and also passes into the human body in the vicinity of the radiation field 2. The scintillating fiber 5 (of conventional composition and having a length of between 0.25 and 2.0 meters and a diameter of between 0.25 and 1.0 mm, with 0.5 mm being preferred) has an insertion end 5a (or tip, which is inserted into the human body) and an external end 5b (which is shown only schematically in FIG. 1 and which remains outside of the human body, being shielded from ambient light e.g. by means of an extramural absorber coating on the scintillating fiber wall, or by encasing the scintillating fiber in a thin wall, opaque, polymer tubing). The external end 5b of the scintillating fiber is optically (and in the preferred embodiments, mechanically) coupled to a light intensity measuring device 6. The light intensity measuring device 6, which in the preferred embodiments comprises a photo-multiplier tube (PMT), is located substantially outside of the radiation field 2 and produces a voltage output 6a in accordance with the magnitude of light intensity emanating from the external end 5b of the scintillating fiber 5. In the preferred embodiments of the invention, the light intensity measuring device 6 responds substantially linearly to incident light and produces a voltage output 6a which is linearly related to, or substantially linearly related to, the dose rate of radiation hitting the scintillating fiber. (The dose rate is proportional to the number of radiation emissions per second.) Semiconductor diode modules may also be employed as the light intensity measuring device 6. Displacing means 7 are provided for inserting the scintillating fiber 5 into and withdrawing the scintillating fiber 5 from the guide channel 4 (and human body) by pushing or pulling. The displacing means 7 may be mechanical (such as a motor coupled to a wheel which linearly drives the scintillating fiber 5) or manual (that is, the movement of the scintillating fiber 5 can be imparted by the hand of an operator). Displacement detecting means 8 are provided for detecting the amount of displacement of the scintillating fiber 5 imparted by the displacing means 7 and producing an output signal 8a representative thereof. The displacement detecting means 8 may comprise any device which is convenient (such as a rotary encoder coupled to a wheel which is driven by the linear movement of the scintillating fiber 5), and is employed to provide information about both the incremental and the absolute position of the internal end sa of the scintillating fiber 5 within the guide channel (and human body).

The voltage output 6a from the light intensity measuring device 6 and the output signal 8a from the displacement detecting means 8 are fed to a processing circuit 9, the function and operation of which is described below. The processing circuit 9 includes an additional input 10 which receives information about the exact 3-dimensional position of the tip of the scintillating fiber within the human body, e.g. relative to a body organ or body region to be irradiated, or relative to the guide channel 4. The input signal 10 is produced by standard medical imaging means (e.g. X-ray or ultrasound) used to locate the tip of the scintillating fiber 5 before and/or at various times during the radiation measurement procedure. The processing circuit 9 also includes an optional but useful calibration input 11, the purpose of which will be described in greater detail below.

The radiation dosimetry method according to a first preferred embodiment of the invention includes the following steps:

inserting the insertion end 4a of the guide channel 4 into a human body 3 so as to provide a substantially fixed path into the human body 3;

inserting the insertion end 5a of the scintillating fiber 5 into the external end 4b of the guide channel and into the human body 3 along the substantially fixed path;

subjecting the insertion end 5a of the scintillating fiber to the radiation field 2;

using the displacement detecting means 8 and/or the input signal 10 from the standard medical imaging means, detecting an initial position $\Lambda$ ("L" in FIG. 1, as indicated by the phantom line) of the insertion end 5a of the scintillating fiber 5 along the substantially fixed path defined by the guide channel 4 within the human body 3 and sending an initial position signal to the processing circuit 9; and using the light intensity measuring device 6, detecting the light intensity emanating from the external end 5b of the scintillating fiber 5, and sending the voltage output 6a (representing both scintillation light from the scintillating fiber 5 and also Cerenkov light) corresponding to the initial position of the insertion end 5a of the scintillating fiber 5 to the processing circuit 9;

storing the initial position signal and its corresponding voltage output 6a in the processing circuit 9;

using the displacing means 7, incrementally displacing (either step-wise or continuously) the insertion end 5a of the scintillating fiber 5 by a small distance $\Delta\Lambda$ ("delta L" in FIG. 1) to a new position $\Lambda+\Delta\Lambda$ along the substantially fixed path;

using the displacement detecting means 8, detecting the change in position $\Delta\Lambda$ of the insertion end 5a of the scintillating fiber 5 along the substantially fixed path and sending a change in position signal to the processing circuit 9 corresponding to the new position; and using the light intensity measuring device 6, detecting the light intensity emanating from the external end 5b of the scintillating fiber 5, and sending the voltage output 6a (representing both scintillation light from the scintillating fiber 5 and also Cerenkov light) corresponding to the new position of the insertion end 5a of the scintillating fiber 5 to the processing circuit 9;

storing the change in position signal and its corresponding voltage output 6a in the processing circuit 9;

in the processing circuit 9, determining a radiation dose rate, substantially free from the effects of Cerenkov light, for an incremental position of the insertion end (or tip) 5a of the scintillating fiber 5 as the insertion end 5a occupies a segment from $\Lambda$ to $\Lambda+\Delta\Lambda$ along the substantially fixed path defined by the guide channel 4 according to the Dose Rate equation:

$$\text{Dose Rate} = C \times \Delta V / \Delta\Lambda, \tag{1}$$

where C is a calibration coefficient (optional), $\Delta V$ is the change in voltage output of the light intensity measuring device which results from the insertion end 5a of the scintillating fiber 5 being moved between the initial and new positions $\Lambda$ and $\Lambda+\Delta\Lambda$, and $\Delta\Lambda$ is the amount of change in position of the insertion end 5a of the scintillating fiber; and repeatedly incrementally displacing the insertion end 5a of the scintillating fiber 5 by a small distance, detecting the change in position of the insertion end 5a of the scintillating fiber 5 and the corresponding light intensity emanating from the scintillating fiber, and determining the corresponding radiation dose rate for each incremental position of the insertion end 5a of the scintillating fiber 5 (i.e. as the insertion end 5a occupies additional incremental segments along the substantially fixed insertion path defined by the guide channel 4) according to the Dose Rate equation (1).

The radiation dosimetry method according to a second preferred embodiment of the invention includes the following steps for providing high-resolution imaging:

inserting the insertion end 4a of the guide channel 4 into a human body 3 so as to provide a substantially fixed path into the human body 3;

inserting the insertion end 5a of the scintillating fiber 5 into the external end 4b of the guide channel and into the human body 3 along the substantially fixed path;

subjecting the insertion end 5a of the scintillating fiber to the radiation field 2;

using the displacement detecting means 8 and/or the input signal 10 from the standard medical imaging means, detecting an initial position Λ ("L" in FIG. 1, as indicated by the phantom line) of the insertion end 5a of the scintillating fiber 5 along the substantially fixed path defined by the guide channel 4 within the human body 3 and sending an initial position signal to the processing circuit 9; and using the light intensity measuring device 6, detecting the light intensity emanating from the external end 5b of the scintillating fiber 5, and sending the voltage output 6a corresponding to the initial position of the insertion end 5a of the scintillating fiber 5 to the processing circuit 9;

storing the initial position signal and its corresponding voltage output 6a in the processing circuit 9;

using the displacing means 7, incrementally displacing (either step-wise or continuously) the insertion end 5a of the scintillating fiber 5 by a small distance ΔΛ ("delta L" in FIG. 1) to a new position Λ+ΔΛ along the substantially fixed path;

using the displacement detecting means 8, detecting the change in position ΔΛ of the insertion end 5a of the scintillating fiber 5 along the substantially fixed path and sending a change in position signal to the processing circuit 9 corresponding to the new position; and using the light intensity measuring device 6, detecting the light intensity emanating from the external end 5b of the scintillating fiber 5, and sending the voltage output 6a corresponding to the new position of the insertion end 5a of the scintillating fiber 5 to the processing circuit 9;

storing the change in position signal and its corresponding voltage output 6a in the processing circuit 9;

in the processing circuit 9, determining a radiation dose rate for an incremental position of the insertion end (or tip) 5a of the scintillating fiber 5 from Λ to Λ+ΔΛ as the insertion end 5a occupies a segment from Λ to Λ+ΔΛ along the substantially fixed path defined by the guide channel 4 according to the Dose Rate equation:

$$\text{Dose Rate} = C \times \Delta V / \Delta \Lambda, \quad (1)$$

where C is a calibration coefficient (optional), ΔV is the change in voltage output of the light intensity measuring device which results from the insertion end 5a of the scintillating fiber 5 being moved between the initial and new positions Λ and Λ+ΔΛ, and ΔΛ is the amount of change in position of the insertion end 5a of the scintillating fiber; and repeatingly incrementally displacing the insertion end 5a of the scintillating fiber 5 by a small distance, detecting the change in position of the insertion end 5a of the scintillating fiber 5 and the corresponding light intensity emanating from the scintillating fiber, and determining the corresponding radiation dose rate for each incremental position of the insertion end 5a of the scintillating fiber 5 (i.e. as the insertion end 5a occupies additional incremental segments along the substantially fixed insertion path defined by the guide channel 4) according to the Dose Rate equation (1).

It will be seen that the above methods provides means to achieve 1-dimensional radiation tomography along an arbitrary (but fixed) curved or straight path. Simple arguments show that the ratio of the change in the external light intensity (measured at the PMT) divided by the displacement of the fiber is proportional to the dose rate at the internal scintillating fiber tip, if the fiber path in the region of the radiation field does not change. Additionally, the derived Dose Rate(s) is/are substantially free from the adverse effects of Cerenkov light (as well as all contributions which are substantially constant during the displacement ΔΛ). This is shown in the following scenario.

Imagine a scintillating fiber having some (unknown but fixed) path within the body, and extending outside the body to a means of measuring light intensity. A measurement of the light (due to fiber irradiation) in the scintillating fiber arriving at the light measuring device is made. Now imagine a small segment of length, ΔΛ, of the scintillating fiber being cut off at the inner tip of the fiber and attached at the outer tip of the fiber which is at the input of the light intensity measuring device, and where the radiation intensity is negligible. A second measurement of light intensity is now made. The difference of the two light intensity measurements, which results from the light generated in 'ΔΛ', is called 'ΔI'. If the light measuring device responds linearly (or substantially linearly) to the incident light, then the Dose Rate equation, given above at (1), results. (A small correction for attenuation of light in the scintillating fiber that results in this process is omitted from the Dose Rate equation. This correction is ~1% (negligible), but can be easily included in the Dose Rate equation. All other contributions to the measured light intensity, which complicate the dosimetry measurement, are removed with this difference measurement. This cancels out, for example, most (~99%) of the Cerenkov radiation generated along the fiber remaining in the body. Only radiation light from the fiber tip survives the difference measurement. Here isotropic scintillation light will greatly outweigh the Cerenkov light.) The Dose Rate equation, with no derived knowledge of the calibration coefficient C (i.e., with no further measurements, and using C=1 in the Dose Rate equation and for the calibration input 11 to the processing circuit 9 in FIG. 1), yields a relative Dose Rate equation useful in finding edges and other features (e.g. local maximums) of radiation fields. On the other hand, if the voltage output of the light intensity measuring device is linearly (or substantially linearly) related to the dose rate of the radiation hitting the scintillating fiber, then C is a constant, and a single calibration measurement will yield the value of C, permitting an absolute Dose Rate to be obtained in all further measurements. This allows measurement of in-vivo radiation without complications from Cerenkov (and other in-fiber) contributions.

In order to obtain absolute Dose Rate values by the above radiation dosimetry method, only one calibration run (to find C in the Dose Rate equation) is usually necessary. This calibration can be carried out in a safe (dummy) material and in an environment where the dose rate is known and where $\Delta V$ and $\Delta\Lambda$ can be sensed or detected. Solving the Dose Rate equation for C (and the use the derived calibration coefficient C for the calibration input 11 to the processing circuit 9 in FIG. 1) is then a straight-forward process.

In the case where the Dose Rate equation is used with a 0.5 mm diameter scintillating fiber and a photo-multiplier tube (PMT) having a gain of $8.5*10^{10}$ V/W, and where the incremental displacement of the scintillating fiber tip 5a is 0.5 mm, then a $\Delta V$ at the PMT output of approximately 2.5 mV will result when the scintillating fiber tip is in a region of a 1 mGray/sec dose rate. This can be measured in approximately 1 second (to provide for averaging with signal integration) or less. If desired, the scintillating fiber can be moved at constant speed and data can be taken periodically; dosimetry can thereby be achieved along the fiber path from the $\Delta V$ signals produced from the PMT output. Measurements of 10 cm paths with sub-mm resolution will take only a few seconds.

This low-cost dosimetry method, usable with small, battery-operated PMTs, has simplicity, smallness, and sufficient responsivity for almost all "in-vivo", measurements. Data logging, computer storage, & fast radiation control are easily achieved. Uniformity of fiber radiation response can be independently measured, if necessary. The use of endoscopes and radio-pharmaceuticals can provide special features and performance benefits in this dosimetry.

While the above invention has been described with certain particularity, it is not meant to be limited to the above described preferred embodiments. Therefore, the invention will encompass the preferred embodiments described above as well as any modifications thereof which will fall within the scope of the appended claims.

I claim:

1. A displacement difference dosimetry method for in-vivo measuring of dose rates within a radiation field, the method comprising the steps of:
   a) providing a scintillating fiber having an insertion end and a coupling end;
   b) coupling the coupling end of the scintillating fiber to a light intensity measuring device, the light intensity measuring device being located substantially outside of the radiation field and producing a voltage output in accordance with a measured light intensity from the scintillating fiber;
   c) providing a guide channel having an insertion end and an external end;
   d) inserting the insertion end of the guide channel into a human body to a region where radiation is to be measured, so as to provide a substantially fixed path into the human body;
   e) inserting the insertion end of the scintillating fiber into the external end of the guide channel and into the human body along the substantially fixed path;
   f) subjecting the region of the body at the insertion end of the scintillating fiber to radiation;
   g) detecting the position $\Lambda$ of the insertion end of the scintillating fiber along the substantially fixed path within the human body and measuring the light intensity at the light intensity measuring device, with the measured light intensity representing both scintillation light from the scintillating fiber and also Cerenkov light;
   h) incrementally displacing the insertion end of the scintillating fiber by a small distance $\Delta\Lambda$ to a new detected position $\Lambda+\Delta\Lambda$ along the substantially fixed path and measuring the light intensity at the light intensity measuring device, with the measured light intensity representing both scintillation light from the scintillating fiber and also Cerenkov light;
   i) determining a radiation dose rate, substantially free from the effects of Cerenkov light, for an incremental segment from $\Lambda$ to $\Lambda+\Delta\Lambda$ along the substantially fixed path according to the expression:

$$\text{Dose Rate} = C \times \Delta V / \Delta\Lambda,$$

where C is a coefficient, $\Delta V$ is the change in voltage output of the light intensity measuring device which results from the insertion end of the scintillating fiber being moved between the positions $\Lambda$ and $\Lambda+\Delta\Lambda$, and $\Delta\Lambda$ is the amount of incremental displacement.

2. The displacement difference dosimetry method as recited in claim 1, further including the step of:
   using C=1 for the coefficient; and
   using the Dose Rate expression to yield a relative dose rate.

3. The displacement difference dosimetry method as recited in claim 1, wherein the voltage output produced by the light intensity measuring device varies substantially linearly in accordance with the dose rate of radiation hitting the scintillating fiber, and the method further includes the steps of:
   deriving the coefficient C as a calibration coefficient in an environment where the dose rate is known and where $\Delta V$ and $\Delta\Lambda$ in the Dose Rate expression can be sensed or detected; and
   using the derived calibration coefficient for the coefficient C in the Dose Rate expression.

4. The displacement difference dosimetry method as recited in claim 1, wherein the guide channel is a catheter which is inserted into the human body.

5. The displacement difference dosimetry method as recited in claim 1, wherein the guide channel is a hypodermic needle which is inserted into the human body.

6. The displacement difference dosimetry method as recited in claim 1, wherein after the radiation dose rate for the incremental segment from $\Lambda$ to $\Lambda+\Delta\Lambda$ along the substantially fixed path has been determined, the following additional step is repeatingly performed to provide 1-dimensional radiation tomography:
   j) incrementally displacing the insertion end of the scintillating fiber by an additional small distance, detecting the resulting change in position of the insertion end of the scintillating fiber and measuring the corresponding light intensity from the scintillating fiber at the light intensity measuring device, and determining a new radiation dose rate for an additional incremental segment along the substantially fixed path according to the Dose Rate expression.

7. A displacement difference dosimetry method for in-vivo measuring of dose rates within a radiation field, the method comprising the steps of:
   a) providing a scintillating fiber having an insertion end and a coupling end;
   b) coupling the coupling end of the scintillating fiber to a light intensity measuring device, the light intensity measuring device being located substantially outside of the radiation field and producing a voltage output which varies substantially linearly in accordance with a dose rate of radiation hitting the scintillating fiber;
   c) providing a guide channel having an insertion end and an external end;

d) inserting the insertion end of the guide channel into a human body to a region where radiation is to be measured, so as to provide a substantially fixed path into the human body;

e) inserting the insertion end of the scintillating fiber into the external end of the guide channel and into the human body along the substantially fixed path;

f) subjecting the region of the body at the insertion end of the scintillating fiber to radiation;

g) detecting the position $\Lambda$ of the insertion end of the scintillating fiber along the substantially fixed path within the human body and measuring the light intensity at the light intensity measuring device, with the measured light intensity representing both scintillation light from the scintillating fiber and also Cerenkov light;

h) incrementally displacing the insertion end of the scintillating fiber by a small distance $\Delta\Lambda$ to a new detected position $\Lambda+\Delta\Lambda$ along the substantially fixed path and measuring the light intensity at the light intensity measuring device, with the measured light intensity representing both scintillation light from the scintillating fiber and also Cerenkov light;

i) determining a radiation dose rate, substantially free from the effects of Cerenkov light, for an incremental segment from $\Lambda$ to $\Lambda+\Delta\Lambda$ along the substantially fixed path according to the expression:

Dose Rate=$C \times \Delta V/\Delta \Lambda$, where C is a coefficient, $\Delta V$ is the change in voltage output of the light intensity measuring device which results from the insertion end of the scintillating fiber being moved between the positions $\Lambda$ and $\Lambda+\Delta\Lambda$, and $\Delta\Lambda$ is the amount of incremental displacement.

8. The displacement difference dosimetry method as recited in claim 7, further including the step of:
using C=1 for the coefficient; and
using the Dose Rate expression to yield a relative dose rate.

9. The displacement difference dosimetry method as recited in claim 7, wherein the guide channel is a catheter which is inserted into the human body.

10. The displacement difference dosimetry method as recited in claim 7, wherein the guide channel is a hypodermic needle which is inserted into the human body.

11. The displacement difference dosimetry method as recited in claim 7, wherein after the radiation dose rate for the incremental segment from $\Lambda$ to $\Lambda+\Delta\Lambda$ along the substantially fixed path has been determined, the following additional step is repeatingly performed to provide 1-dimensional radiation tomography:

j) incrementally displacing the insertion end of the scintillating fiber by an additional small distance, detecting the resulting change in position of the insertion end of the scintillating fiber and measuring the corresponding light intensity from the scintillating fiber at the light intensity measuring device, and determining a new radiation dose rate for an additional incremental segment along the substantially fixed path according to the Dose Rate expression.

12. A displacement difference dosimetry method for in-vivo measuring of dose rates within a radiation field, the method comprising the steps of:

a) providing a scintillating fiber having an insertion end and a coupling end;

b) coupling the coupling end of the scintillating fiber to a light intensity measuring device, the light intensity measuring device being located substantially outside of the radiation field and producing a voltage output which varies substantially linearly in accordance with a dose rate of radiation hitting the scintillating fiber;

c) providing a guide channel having an insertion end and an external end;

d) inserting the insertion end of the guide channel into a human body to a region where radiation is to be measured, so as to provide a substantially fixed path into the human body;

e) inserting the insertion end of the scintillating fiber into the external end of the guide channel and into the human body along the substantially fixed path;

f) subjecting the region of the body at the insertion end of the scintillating fiber to radiation;

g) detecting the position $\Lambda$ of the insertion end of the scintillating fiber along the substantially fixed path within the human body and measuring the light intensity at the light intensity measuring device;

h) incrementally displacing the insertion end of the scintillating fiber by a small distance $\Delta\Lambda$ to a new detected position $\Lambda+\Delta\Lambda$ along the substantially fixed path and measuring the light intensity at the light intensity measuring device;

i) determining a radiation dose rate for an incremental segment from $\Lambda$ to $\Lambda+\Delta\Lambda$ along the substantially fixed path according to the expression:

Dose Rate=$C \times \Delta V/\Delta \Lambda$, where C is a coefficient, $\Delta V$ is the change in voltage output of the light intensity measuring device which results from the insertion end of the scintillating fiber being moved between the positions $\Lambda$ and $\Lambda+\Delta\Lambda$, and $\Delta\Lambda$ is the amount of incremental displacement; and after the radiation dose rate for the incremental segment from $\Lambda$ to $\Lambda+\Delta\Lambda$ along the substantially fixed path has been determined, repeatingly performing the following additional step to provide 1-dimensional radiation tomography:

j) incrementally displacing the insertion end of the scintillating fiber by an additional small distance, detecting the resulting change in position of the insertion end of the scintillating fiber and measuring the corresponding light intensity from the scintillating fiber at the light intensity measuring device, and determining a new radiation dose rate for an additional incremental segment along the substantially fixed path according to the Dose Rate expression.

13. The displacement difference dosimetry method as recited in claim 12, further including the step of:
using C=1 for the coefficient; and
using the Dose Rate expression to yield a relative dose rate.

14. The displacement difference dosimetry method as recited in claim 12, wherein the method further includes the steps of:
deriving the coefficient C as a calibration coefficient in an environment where the dose rate is known and where $\Delta V$ and $\Delta\Lambda$ in the Dose Rate expression can be sensed or detected; and
using the derived calibration coefficient for the coefficient C in the Dose Rate expression.

15. The displacement difference dosimetry method as recited in claim 12, wherein the guide channel is a catheter which is inserted into the human body.

16. The displacement difference dosimetry method as recited in claim 12, wherein the guide channel is a hypodermic needle which is inserted into the human body.

17. A displacement difference dosimetry method for in-vivo measuring of dose rates within a radiation field, the method comprising the steps of:
   a) providing a flexible scintillating fiber having an insertion end and a coupling end, the scintillating fiber having at least one cladding layer and a length of between 0.25 meters and 2.0 meters;
   b) coupling the coupling end of the scintillating fiber to a light intensity measuring device, the light intensity measuring device being located substantially outside of the radiation field and producing a voltage output in accordance with a measured light intensity from the scintillating fiber;
   c) providing a guide channel having an insertion end and an external end;
   d) inserting the insertion end of the guide channel into a human body to a region where radiation is to be measured, so as to provide a substantially fixed path into the human body;
   e) inserting the insertion end of the scintillating fiber into the external end of the guide channel and into the human body along the substantially fixed path;
   f) subjecting the region of the body at the insertion end of the scintillating fiber to radiation capable of producing Cerenkov light in the scintillating fiber while the coupling end of the scintillating fiber remains outside the human body and shielded from ambient light;
   g) detecting an initial position $\Lambda$ of the insertion end of the scintillating fiber along the substantially fixed path within the human body, and measuring the light intensity at the light intensity measuring device, with the measured light intensity representing both scintillation light from the scintillating fiber and also Cerenkov light produced in the scintillating fiber when the insertion end is at the initial position;
   h) storing in a processing circuit signals representative of the initial position $\Lambda$ of the insertion end of the scintillating fiber along the substantially fixed path within the human body, and the measured light intensity at the light intensity measuring device when the insertion end of the scintillating fiber is at the initial position;
   i) incrementally displacing the insertion end of the scintillating fiber by a small distance $\Delta\Lambda$ to a new detected position $\Lambda+\Delta\Lambda$ along the substantially fixed path and measuring the light intensity at the light intensity measuring device, with the measured light intensity representing both scintillation light from the scintillating fiber and also Cerenkov light produced in the scintillating fiber when the insertion end is at the new detected position;
   j) in the processing circuit, determining a radiation dose rate, substantially free from the effects of Cerenkov light, for an incremental segment from $\Lambda$ to $\Lambda+\Delta\Lambda$ along the substantially fixed path according to the expression:

Dose Rate=$C \times \Delta V/\Delta\Lambda$, where C is a coefficient, $\Delta V$ is a change in voltage output of the light intensity measuring device which results from the insertion end of the scintillating fiber being moved between the positions $\Lambda$ and $\Lambda+\Delta\Lambda$, and $\Delta\Lambda$ is the amount of incremental displacement.

18. The displacement difference dosimetry method as recited in claim 17, wherein the flexible scintillating fiber is a single, continuous flexible scintillating fiber extending from the insertion end to the coupling end thereof.

19. The displacement difference dosimetry method as recited in claim 17, wherein the voltage output produced by the light intensity measuring device varies substantially linearly in accordance with the dose rate of radiation hitting the scintillating fiber, and the method further includes the steps of:
   deriving the coefficient C as a calibration coefficient in an environment where the dose rate is known and where $\Delta V$ and $\Delta\Lambda$ in the Dose Rate expression can be sensed or detected; and
   using the derived calibration coefficient for the coefficient C in the Dose Rate expression.

20. The displacement difference dosimetry method as recited in claim 17, wherein after the radiation dose rate for the incremental segment from $\Lambda$ to $\Lambda+\Delta\Lambda$ along the substantially fixed path has been determined, the following additional step is repeatingly performed to provide 1-dimensional radiation tomography:
   j) incrementally displacing the insertion end of the scintillating fiber by an additional small distance, detecting the resulting change in position of the insertion end of the scintillating fiber and measuring the corresponding change in light intensity from the scintillating fiber at the light intensity measuring device, and determining a new radiation dose rate for an additional incremental segment along the substantially fixed path according to the Dose Rate expression.

21. A displacement difference dosimetry method for in-vivo measuring of dose rates within a radiation field, the method comprising the steps of:
   a) providing a flexible scintillating fiber having an insertion end and a coupling end, the flexible scintillating fiber having a diameter of between 0.25 mm and 1.0 mm;
   b) coupling the coupling end of the scintillating fiber to a light intensity measuring device, the light intensity measuring device being located substantially outside of the radiation field and producing a voltage output in accordance with a measured light intensity from the scintillating fiber;
   c) providing a guide channel having an insertion end and an external end;
   d) inserting the insertion end of the guide channel into a human body to a region where radiation is to be measured, so as to provide a substantially fixed path into the human body;
   e) inserting the insertion end of the scintillating fiber into the external end of the guide channel and into the human body along the substantially fixed path;
   f) subjecting the region of the body at the insertion end of the scintillating fiber to radiation capable of producing Cerenkov light in the scintillating fiber while the coupling end of the scintillating fiber remains outside the human body and shielded from ambient light;
   g) detecting an initial position $\Lambda$ of the insertion end of the scintillating fiber along the substantially fixed path within the human body, and measuring the light intensity at the light intensity measuring device, with the measured light intensity representing both scintillation light from the scintillating fiber and also Cerenkov light produced in the scintillating fiber when the insertion end is at the initial position;
   h) storing in a processing circuit signals representative of the initial position $\Lambda$ of the insertion end of the scintillating fiber along the substantially fixed path within the human body, and the measured light intensity at the light intensity measuring device when the insertion end of the scintillating fiber is at the initial position;

i) incrementally displacing the insertion end of the scintillating fiber by a small distance $\Delta\Lambda$ to a new detected position $\Lambda+\Delta\Lambda$ along the substantially fixed path and measuring the light intensity at the light intensity measuring device, with the measured light intensity representing both scintillation light from the scintillating fiber and also Cerenkov light produced in the scintillating fiber when the insertion end is at the new detected position;

j) in the processing circuit, determining a radiation dose rate, substantially free from the effects of Cerenkov light, for an incremental segment from $\Lambda$ to $\Lambda+\Delta\Lambda$ along the substantially fixed path according to the expression:

Dose Rate=$C\times\Delta\Lambda$, where C is a coefficient, $\Delta V$ is a change in voltage output of the light intensity measuring device which results from the insertion end of the scintillating fiber being moved between the positions $\Lambda$ and $\Lambda+\Delta\Lambda$, and $\Delta\Lambda$ is the amount of incremental displacement.

22. The displacement difference dosimetry method as recited in claim 21, wherein the flexible scintillating fiber is a single, continuous flexible scintillating fiber extending from the insertion end to the coupling end thereof.

23. The displacement difference dosimetry method as recited in claim 21, wherein the voltage output produced by the light intensity measuring device varies substantially linearly in accordance with the dose rate of radiation hitting the scintillating fiber, and the method further includes the steps of:

deriving the coefficient C as a calibration coefficient in an environment where the dose rate is known and where $\Delta V$ and $\Delta\Lambda$ in the Dose Rate expression can be sensed or detected; and using the derived calibration coefficient for the coefficient C in the Dose Rate expression.

24. The displacement difference dosimetry method as recited in claim 21, wherein after the radiation dose rate for the incremental segment from $\Lambda$ to $\Lambda+\Delta\Lambda$ along the substantially fixed path has been determined, the following additional step is repeatingly performed to provide 1-dimensional radiation tomography:

j) incrementally displacing the insertion end of the scintillating fiber by an additional small distance, detecting the resulting change in position of the insertion end of the scintillating fiber and measuring the corresponding change in light intensity from the scintillating fiber at the light intensity measuring device, and determining a new radiation dose rate for an additional incremental segment along the substantially fixed path according to the Dose Rate expression.

25. A displacement difference dosimetry method for in-vivo measuring of dose rates within a radiation field, the method comprising the steps of:

a) providing a flexible scintillating fiber having an insertion end and an external end;

b) optically and mechanically coupling the external end of the scintillating fiber to a light intensity measuring device, the light intensity measuring device comprising a photomultiplier tube which is located substantially outside of the radiation field so as to produce a voltage output which varies in accordance with a dose rate of radiation hitting the scintillating fiber;

c) providing a guide channel having an insertion end and an external end;

d) providing a processing circuit;

e) inserting the insertion end of the guide channel into a human body to a region where radiation is to be measured, so as to provide a substantially fixed path into the human body;

f) inserting the insertion end of the scintillating fiber into the external end of the guide channel and into the human body along the substantially fixed path;

g) subjecting the region of the body at the insertion end of the scintillating fiber to radiation while the external end of the scintillating fiber remains outside the human body, the external end of the scintillating fiber being shielded from ambient light;

h) detecting an initial position $\Lambda$ of the insertion end of the scintillating fiber along the substantially fixed path within the human body and sending an initial position signal to the processing circuit;

i) measuring the light intensity emanating from the external end of the flexible scintillating fiber at the light intensity measuring device when the insertion end is at the initial position, and sending a voltage output from the light intensity measuring device to the processing circuit;

j) storing the initial position signal and the corresponding voltage output from the light intensity measuring device in the processing circuit;

k) incrementally displacing the insertion end of the scintillating fiber by a small distance $\Delta\Lambda$ to a new detected position $\Lambda+\Delta\Lambda$ along the substantially fixed path and measuring the light intensity at the light intensity measuring device;

l) in the processing circuit, determining a radiation dose rate for an incremental segment from $\Lambda$ to $\Lambda+\Delta\Lambda$ along the substantially fixed path according to the expression:

Dose Rate=$C\times\Delta V/\Delta\Lambda$, where C is a coefficient, $\Delta V$ is the change in voltage output of the light intensity measuring device which results from the insertion end of the scintillating fiber being moved between the initial position $\Lambda$ and the new detected position $\Lambda+\Delta\Lambda$, and $\Delta\Lambda$ is the amount of incremental displacement; and after the radiation dose rate for the incremental segment from $\Lambda$ to $\Lambda+\Delta\Lambda$ along the substantially fixed path has been determined, repeatingly performing the following additional step to provide 1-dimensional radiation tomography;

m) incrementally displacing the insertion end of the scintillating fiber by an additional small distance, detecting the resulting change in position of the insertion end of the scintillating fiber and measuring the corresponding change in light intensity from the scintillating fiber at the light intensity measuring device, and determining a new radiation dose rate for an additional incremental segment along the substantially fixed path according to the Dose Rate expression.

26. The displacement difference dosimetry method as recited in claim 25, wherein the voltage output produced by the light intensity measuring device varies substantially linearly in accordance with the dose rate of radiation hitting the scintillating fiber, and the method further includes the steps of:

deriving the coefficient C as a calibration coefficient in an environment where the dose rate is known and where $\Delta V$ and $\Delta \Lambda$ in the Dose Rate expression can be sensed or detected; and using the derived calibration coefficient for the coefficient C in the Dose Rate expression.

27. The displacement difference dosimetry method as recited in claim 1, wherein the step of providing the scintillating fiber further includes:

providing the scintillating fiber with at least one cladding layer for greatly reducing a loss of light within the scintillating fiber.

28. The displacement difference dosimetry method as recited in claim 7, wherein the step of providing the scintillating fiber further includes:

providing the scintillating fiber with at least one cladding layer for greatly reducing a loss of light within the scintillating fiber.

29. The displacement difference dosimetry method as recited in claim 12, wherein the step of providing the scintillating fiber further includes:

providing the scintillating fiber with at least one cladding layer for greatly reducing a loss of light within the scintillating fiber.

30. The displacement difference dosimetry method as recited in claim 21, wherein the step of providing the flexible scintillating fiber further includes:

providing the flexible scintillating fiber with at least one cladding layer for greatly reducing a loss of light within the scintillating fiber.

31. The displacement difference dosimetry method as recited in claim 25, wherein the step of providing the flexible scintillating fiber further includes:

providing the flexible scintillating fiber with at least one cladding layer for greatly reducing a loss of light within the scintillating fiber.

32. The displacement difference dosimetry method as recited in claim 1, wherein the step of subjecting the region of the body at the insertion end of the scintillating fiber to radiation further includes:

subjecting the region of the body at the insertion end of the scintillating fiber to radiation while the coupling end of the scintillating fiber remains outside the human body and shielded from ambient light.

33. The displacement difference dosimetry method as recited in claim 7, wherein the step of subjecting the region of the body at the insertion end of the scintillating fiber to radiation further includes:

subjecting the region of the body at the insertion end of the scintillating fiber to radiation while the coupling end of the scintillating fiber remains outside the human body and shielded from ambient light.

34. The displacement difference dosimetry method as recited in claim 12, wherein the step of subjecting the region of the body at the insertion end of the scintillating fiber to radiation further includes:

subjecting the region of the body at the insertion end of the scintillating fiber to radiation while the coupling end of the scintillating fiber remains outside the human body and shielded from ambient light.

* * * * *

UNITED STATES PATENT AND TRADEMARK OFFICE
CERTIFICATE OF CORRECTION

PATENT NO.    : 6,993,376 B2
DATED         : January 31, 2006
INVENTOR(S)   : Louis R. Testardi It is certified that error appears in the above-identified patent and that said Letters Patent is hereby corrected as shown below:

Column 3,
Lines 3, 11, 22, 59 and 64, replace "$\Lambda$" with -- $\ell$ --.
Lines 12 and 65 (both occurrences), replace "$\Lambda$" with -- $\ell$ --.
Lines 19 and 27 (all occurrences), replace "$\Lambda$" with -- $\ell$ --.

Column 4,
Line 4, replace "$\Lambda$" with -- $\ell$ --.
Lines 2 and 9 (all occurrences), replace "$\Lambda$" with -- $\ell$ --.
Line 12, "$\Lambda$ to $1+\Delta\Lambda$" should be -- $\ell$ to $\ell+\Delta\ell$ --.

Column 6,
Lines 14, 31, 35 and 56, replace "$\Lambda$" with -- $\ell$ --.
Lines 32, 53 and 62 (all occurrences), replace "$\Lambda$" with -- $\ell$ --.

Column 7,
Lines 21, 37 and 41, replace "$\Lambda$" with -- $\ell$ --.
Line 38 (both occurrences), replace "$\Lambda$" with -- $\ell$ --.
Lines 55, 56, and 66 (all occurrences), replace "$\Lambda$" with -- $\ell$ --.

Column 8,
Lines 23, 29 and 35, replace "$\Lambda$" with -- $\ell$ --.

Column 9,
Lines 2, 57 and 65, replace "$\Lambda$" with -- $\ell$ --.
Line 66, (both occurrences), replace "$\Lambda$" with -- $\ell$ --.

Column 10,
Lines 9 and 29, replace "$\Lambda$" with -- $\ell$ --.
Lines 6, 13 and 41 (all occurrences), replace "$\Lambda$" with -- $\ell$ --.

UNITED STATES PATENT AND TRADEMARK OFFICE
CERTIFICATE OF CORRECTION

PATENT NO.     : 6,993,376 B2
DATED          : January 31, 2006
INVENTOR(S)    : Louis R. Testardi It is certified that error appears in the above-identified patent and that said Letters Patent is hereby corrected as shown below:

Column 11,
Lines 10, 18 and 29, replace "Λ" with -- $\ell$ --.
Line 19 (both occurrences), replace "Λ" with -- $\ell$ --.
Lines 26, 33 and 48, (all occurrences), replace "Λ" with -- $\ell$ --.

Column 12,
Lines 17, 22, 29 and 61, replace "Λ" with -- $\ell$ --.
Line 23 (both occurrences), replace "Λ" with -- $\ell$ --.
Line 27, 34 and 37 (all occurrences), replace "Λ" with -- $\ell$ --.

Column 13,
Lines 31, 40, 46 and 59, replace "Λ" with -- $\ell$ --.
Lines 47 (both occurrences), replace "Λ" with -- $\ell$ --.
Lines 56 and 64 (all occurrences), replace "Λ" with -- $\ell$ --.

Column 14,
Lines 11, 57 and 66, replace "Λ" with -- $\ell$ --.
Line 17 (all occurrences), replace "Λ" with -- $\ell$ --.

Column 15,
Lines 5, 18 and 37, replace "Λ" with -- $\ell$ --.
Line 6, (both occurrences), replace "Λ" with -- $\ell$ --.
Lines 15, 23 and 43 (all occurrences), replace "Λ" with -- $\ell$ --.

Column 16,
Lines 18, 33, 41 and 46, replace "Λ" with -- $\ell$ --.
Line 34 (both occurrences), replace "Λ" with -- $\ell$ --.
Lines 39, 47 and 50, (all occurrences), replace "Λ" with -- $\ell$ --.

UNITED STATES PATENT AND TRADEMARK OFFICE
CERTIFICATE OF CORRECTION

PATENT NO. : 6,993,376 B2 Page 3 of 3
DATED : January 31, 2006
INVENTOR(S) : Louis R. Testardi It is certified that error appears in the above-identified patent and that said Letters Patent is hereby corrected as shown below:

Column 17,
Line 5, replace "Λ" with -- $\ell$ --.

Signed and Sealed this

Thirteenth Day of June, 2006

JON W. DUDAS
*Director of the United States Patent and Trademark Office*